(12) United States Patent
Maendel

(10) Patent No.: US 11,738,350 B2
(45) Date of Patent: *Aug. 29, 2023

(54) PRODUCT HAVING CALCIFIED EGG SHELL PARTICLES HAVING DIAMETER OF 3 MICRONS OR LESS

(71) Applicant: Jack Maendel, Morris (CA)

(72) Inventor: Jack Maendel, Morris (CA)

(73) Assignee: Eggshellerate Inc., Morris (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/649,399

(22) Filed: Jan. 31, 2022

(65) Prior Publication Data

US 2022/0152624 A1  May 19, 2022

Related U.S. Application Data

(60) Division of application No. 16/593,855, filed on Oct. 4, 2019, now Pat. No. 11,266,997, which is a continuation of application No. PCT/CA2018/050440, filed on Apr. 10, 2018.

(60) Provisional application No. 62/483,757, filed on Apr. 10, 2017.

(51) Int. Cl.
*B02C 23/12* (2006.01)
*B02C 23/14* (2006.01)
*C01F 11/18* (2006.01)
*A01K 43/00* (2006.01)

(52) U.S. Cl.
CPC .............. *B02C 23/12* (2013.01); *B02C 23/14* (2013.01); *C01F 11/18* (2013.01); *A01K 43/005* (2013.01); *B02C 2201/06* (2013.01); *C01P 2004/61* (2013.01)

(58) Field of Classification Search
None
See application file for complete search history.

(56) References Cited

U.S. PATENT DOCUMENTS

| 8,418,943 B2 | 4/2013 | Dejong et al. | |
| 2006/0062857 A1* | 3/2006 | Suzuki | A61K 35/57 |
| | | | 424/687 |
| 2014/0356450 A1* | 12/2014 | Atomi | A61P 43/00 |
| | | | 424/581 |

FOREIGN PATENT DOCUMENTS

| CN | 105902398 A | 8/2016 |
| EP | 0770649 A1 | 5/1997 |
| JP | 2011256260 A | 12/2011 |
| WO | WO 2016/066718 | * 5/2016 |

* cited by examiner

*Primary Examiner* — Ronak C Patel
(74) *Attorney, Agent, or Firm* — Cochran Freund & Young LLC; William W. Cochran

(57) ABSTRACT

Disclosed herein are systems and methods for processing waste egg shells into (i) a first product including calcified egg shell particles having diameters of 3μ or less, and (ii) a second product including calcified egg shell particles having diameters in a range from about 3μ to about 7μ. The first product may be used as a $CaCO_3$ substitute for paint compositions and plastics compositions. The second product may be used as a $CaCO_3$ blasting media substitute for use with abrasive blasting equipment.

1 Claim, 7 Drawing Sheets

PRODUCT HAVING CALCIFIED EGG SHELL PARTICLES HAVING DIAMETER OF 3 MICRONS OR LESS

TECHNICAL FIELD

This disclosure generally relates to processing of waste egg shells. More specifically, this disclosure pertains to systems and methods for separating membranes from egg shells and then processing de-membranized egg shells into fractions suitable for use as $CaCO_3$ filler substitutes for paints, resins, topical compositions, and for use as abrasive blasting media.

BACKGROUND

The increasing volumes of eggs used for large-scale commercial production of egg-based fast foods and food products, baking and cooking ingredients, and the like is resulting in large accumulations of waste egg shells. There have been many attempts to derive products from waste egg shells and some small-scale commercial activities have resulted in separation of the inner membranes from the outer calcified shell components of egg shells. Separated and purified egg shell membranes have been incorporated into oral supplements and topical lotions and creams based on the high levels of collagen and other useful proteins in the membranes. The calcified outer egg shell components are typically ground into coarse and fine granules that are most commonly incorporated into poultry and animal feeds and feed supplements. Alternatively, ground calcified outer egg shell components can be used as soil agronomic supplements and amendments.

Although useful products can be derived from processing waste egg shells, the problem is that the prices consumers are willing to pay for products comprising ground calcified egg shell granules are not sufficiently high enough to cover the costs of processing and producing these types of products. Consequently, the vast majority of commercially produced waste egg shells is simply disposed of in garbage dumps and landfill sites.

SUMMARY

The embodiments of the present disclosure generally relate to systems and methods for processing waste egg shells into commercially useful products.

One embodiment of the present disclosure pertains to systems comprising a plurality of equipment configured for cooperatively receiving waste egg shells, washing the waste egg shells, separating the membrane components from the calcified solids components of the egg shells, washing the de-membranized calcified solids components, drying the de-membranized calcified solids components, milling the dried calcified solids components, separating out three fractions of milled calcified solids components wherein the first fraction comprises calcified particles having a diameter of three microns or less, the second fraction comprises calcified particles having diameters from the range of about three microns to seven microns, and the third fraction comprises calcified particles having diameters greater than seven microns, re-milling the third fraction and separating out the first and second fractions until no more of the third fraction remains, and separately collecting the first fraction and the second fraction. An aspect of this embodiment pertains to separately collecting the membrane components after the separation of the membrane components from egg shell calcified solids components.

An embodiment of the present disclosure pertains to methods for processing waste eggs shells to separate out and collect: (i) a first product comprising calcified solids particles having a diameter of three microns or less, and (ii) a second product comprising calcified particles having diameters from the range of about three microns to seven microns. An aspect of this embodiment pertains to methods that additionally comprise collection of a third product comprising membrane components separated from waste egg shells.

Another embodiment of the present disclosure pertains to packaging of the first egg shell calcified solids particle product for use as a filler in resinous polymer compositions such as epoxy resins, vinylester resins, polyester resins, and the like. The first egg shell calcified solids particle product may also be packaged for use as a filler in paint compositions such as latex paints, alkyd paints, and the like. An aspect of this embodiment pertains to resinous polymer compositions comprising the first egg shell calcified solids particle product. Another aspect of this embodiment pertains to paint compositions comprising the first egg shell calcified particle solids product.

Another embodiment of the present disclosure pertains to packaging of the second egg shell calcified solids particle product for use as a blasting media with abrasive blasting equipment for cleaning and removal of surface coverings from underlying solid surfaces and articles.

Another embodiment of the present disclosure pertains to packaging of the third product comprising the egg shell membrane components, for further processing to produce collagen-based products therefrom.

BRIEF DESCRIPTION OF THE FIGURES

The embodiments of the present disclosure will be described with reference to the following drawings in which.

DETAILED DESCRIPTION

Figure 1:
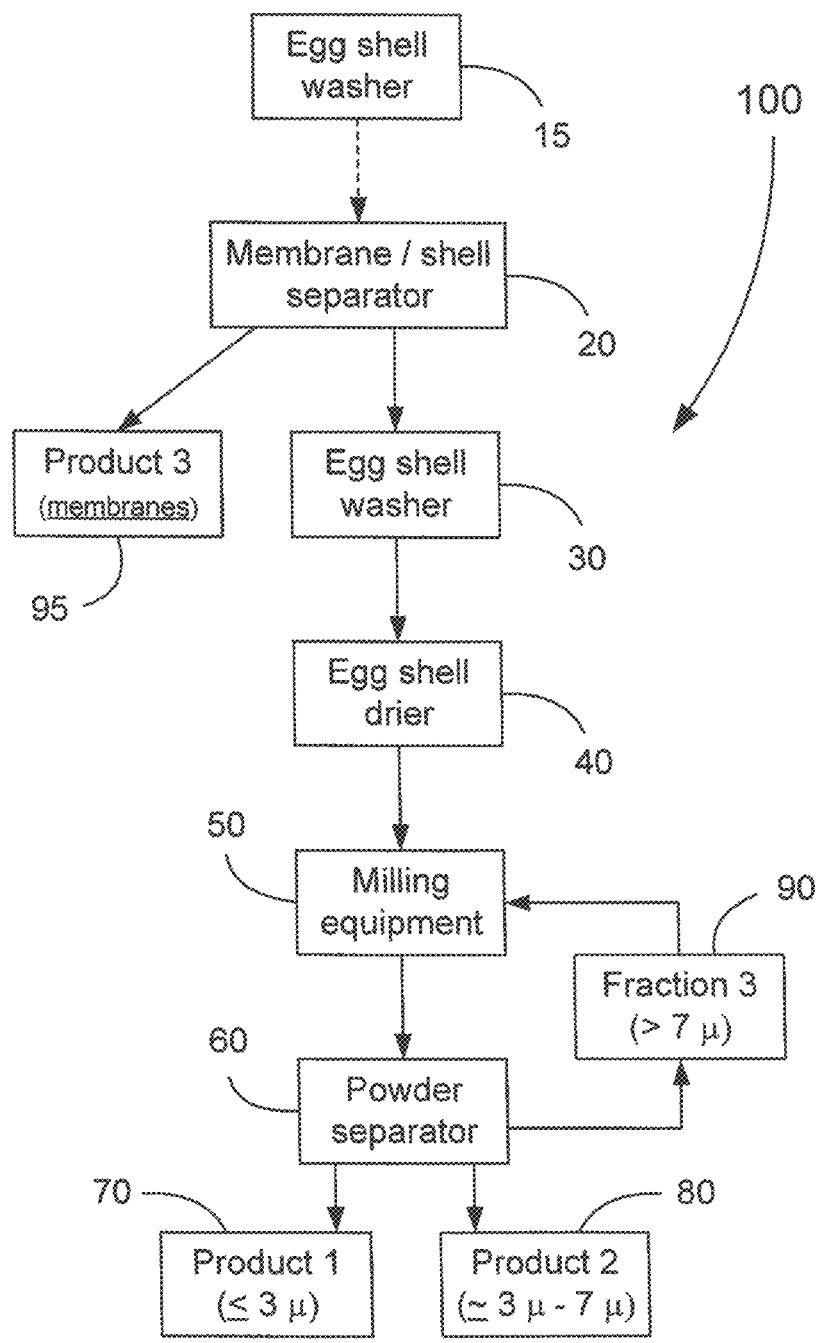
FIG. 1 is a schematic diagram illustrating an example of a waste egg shell processing system according to one embodiment of the present disclosure.

We have surprisingly discovered that egg shells from which the membranes components have been removed, can be milled to produce two very-fine-powdered fractions referred to herein as egg shell calcified particles, that can be used to substitute for chemically synthesized or chemically derived calcium carbonate ($CaCO_3$) and for pulverized quarried or mined limestone in various industrial applications. The first fraction i.e., product, comprises egg shell calcified particles having a particle size of $3\mu$ or less, while the second fraction i.e., product, comprises egg shell calcified particles having particle sizes from a range of about $3\mu$ to $7\mu$.

Consumers are becoming increasingly desirous of products that have reduced contents of chemically synthesized or chemically derived constituents. Industrial manufacturers of, for example, constituents for incorporation into paint compositions and plastics compositions, are trying to satisfy such consumer interest by substituting for the chemically synthesized or chemically derived constituents with suitable naturally occurring components or with physically modified naturally occurring components (i.e., not by chemical processing). Additionally, manufacturers of such products are looking for ingredients by which they can reduce their carbon footprint, for example, by using ingredients with reduced requirements for processing thereby requiring less energy, and/or which do not originate from chemical synthesis manufacturing processes.

Most of the $CaCO_3$ used in industry is extracted from mined or quarried limestone which is then crushed and sieved to provide crushed limestone grains having selected ranges of mesh sizes. However, limestone contains other mineral and organic components which tend to make crushed limestone unsuitable for incorporation into paint and plastics compositions. These industries use precipitated $CaCO_3$ that is produced from calcium oxide dispersed in water through which is then passed carbon dioxide to precipitate out $CaCO_3$. There is a growing segment of paint formulators and manufacturers that are replacing some of the precipitated $CaCO_3$ with clays and/or talcs and are referring to their paints as "ecopaints" of "biopaints". Plastics manufacturers have long used plant-derived materials such as starch, cellulose and proteins to replace some or all of the petroleum-based polymers in their formulations, and commonly refer to such plastics as bioplastics or ecoplastics. However, precipitated $CaCO_3$ is commonly used as a filler in plastics comprising plant-derived polymers.

We have discovered that egg shell calcified particles having a particle size of $3\mu$ or less produced by the methods disclosed herein, can be used as a replacement for precipitated $CaCO_3$ and clays and talcs in paint compositions. We have also discovered that egg shell calcified particles having a particle size of $3\mu$ or less produced by the methods disclosed herein, can be used as a replacement for precipitated $CaCO_3$ as a filler for formulating plastics compositions. Furthermore, such egg shell calcified particles can be substituted as fillers for precipitated $CaCO_3$ in any other application wherein precipitated $CaCO_3$ is used, for example sealers, glues, and the like.

Crushed $CaCO_3$ produced from quarried or mined limestone is commonly used as a blasting media for gentle abrasive cleaning and stripping of coverings on solid surfaces and substrates wherein the coverings are one or more of paint, varnish, rust, grime, soot, oil films, spray-painted graffiti, and the like. The particle i.e., grain sizes of commercially available crushed $CaCO_3$ blasting media are typically in the range of 70 mesh ($210\mu$) to 130 mesh ($115\mu$) with a hardness rating of 2-3 Mohs medium. We have found that egg shell calcified particles from a range of about $3\mu$ to $7\mu$ are well-suited for use with abrasive blasting equipment as a substitute for crushed $CaCO_3$ blasting media and that the smaller egg shell calcified particle size (i.e., $3\mu$ to $7\mu$) provides a softer i.e., more gentle cleaning and stripping function when used with abrasive blasting equipment. Furthermore, such egg shell calcified particles can be substituted as fillers for crushed $CaCO_3$ in any other application wherein crushed $CaCO_3$ is used, for example paints, composites, sealers, glues, and the like.

Accordingly, one embodiment of the present disclosure pertains to a method for processing waste egg shells to produce therefrom two egg shell calcified particle products wherein one product comprises egg shell calcified particles having a diameter of $3\mu$ (~4000 mesh) or less, and is suitable for use as a $CaCO_3$ substitute in paint compositions, plastics compositions, topical cosmetics compositions, and dental filling compositions, and the second product comprises egg shell calcified particles having diameters from a range of about $3\mu$ (~4000 mesh) to $7\mu$ (~1900 mesh) and is suitable for use as a blasting media with abrasive blasting equipment.

The methods according to this disclosure generally comprise the steps of:

1. separating the membrane components of waste egg shells from the calcified outer shell components to produce de-membranized egg shell calcified components.
   It is optional if so desired, to provide a pre-processing waste egg shell washing step to remove any egg yolk and/or egg white residues that may be present on the inner-facing surfaces of the egg shells.
2. washing the de-membranized egg shell calcified components to remove any remaining membrane components, then drying the washed de-membranized egg shell calcified components.
3. milling the dried de-membranized egg shell calcified components to produce small-diameter particles therefrom.
4. separating the milled small-diameter egg shell calcified particles into three fractions wherein the first fraction comprises particles having diameters of $3\mu$ or less, the second fraction comprises particles having diameters in a range from about $3\mu$ to about $7\mu$, and the third fraction comprises particles having diameters greater than $7\mu$.
5. re-milling the third fraction and then separating additional quantities of the first fraction the second fraction, and if necessary, the third fraction.
6. repeating step 5 as many times as necessary to eliminate egg shell calcified particles with diameters greater than $7\mu$.
7. separately packaging the first fraction i.e. the first product and the second fraction i.e. the second product.
   Suitable packaging may include:
   paper bags, for example the bags may be sized to sealably contain 0.5 lb, 1 lb, 2 lb, 2.5 lb, 3 lb, 4 lb, 5 lb, 10 lb, 25 lb, 50 lb, 100 lb, and therebetween,
   bottles, for example the bottles may be sized to contain 50 g, 100 g, 250 g, 500 g, 1 kg, 5 kg, and therebetween,
   pails, for example the pails may be sized to contain 10 lb, 25 lb, 50 lb, and therebetween,
   drums, for example the drums may be sized to contain 25 lb, 50 lb, 75 lb, 100 lb, 200 lbs, and therebetween, bulk bags, for example the bulk bags may be sized to contain ¼ tonne, ½ tonne, ¾ tonne, 1 tonne, and therebetween, However, it is within the scope of this disclosure to use any suitable packaging for separately containing therein the first product or the second product.

The present methods optionally comprise one or more additional steps of collecting and packaging the membrane components separated in step 1, for use in other types of applications.

Another embodiment of the present disclosure pertains to systems comprising a plurality of equipment configured for cooperatively processing waste egg shells into a first product comprising egg shell calcified particles having diameters of 3µ or less, a second product comprising egg shell calcified particles having diameters in a range from about 3µ to about 7µ and optionally, a third product comprising membrane components separated from waste egg shells.

It is to be noted that the methods may be batch methods wherein a selected batch size of waste egg shells is prepared and then processed to output the first product, the second product, and optionally, the third product. Alternatively, the methods may be continuous methods wherein a constant supply of waste egg shells is delivered to the first step of the method and constant outputs of the first product, the second product, and optionally the third product are collected and packaged. Alternatively, the methods may be semi-continuous methods wherein a constant supply of waste egg shells is delivered to the first step of the method for an extended period of time for example 2 h, 3, 4, 6, 8, 12, 18, and therebetween, during which time constant outputs of the first product, the second product, and optionally the third product are collected and packaged.

An example of a system 10 according to the present disclosure is illustrated in FIG. 1, and generally comprises five primary components.

The first primary component 20 is equipment for separating membranes from waste egg shells. Such equipment is known and publically disclosed, for example, in U.S. Pat. Nos. 8,418,943, 8,448,884, 9,370,778 among others. It is optional, if so desired, provide a suitable industrial washing machine 15 to remove residual egg yolk and/or egg white from the inner surfaces of the waste egg shells prior to transfer of the waste egg shells into the membrane separation equipment.

The second primary component is a suitable industrial washing machine 30 to separate any residual membrane from the egg shells that was not completely removed by the membrane separation equipment 20. This washing machine 30 may be the same as the first washing machine 15 or not.

The third primary component is a suitable industrial drier 40 for drying therein the wash de-membranized egg shells. It is within the scope of the present invention to incorporate into the system 10 any of a tray drier, a tumble drier, a centrifugal dewatering machine, an air jet drier, and the like.

The fourth primary component is a suitable milling machine 50 for powderizing the egg shell fragments into very fine particulates.

The fifth primary component is a powder separator 60 to separate out and deliver the first fraction into a collection container 70 for receiving product 1 comprising egg shell calcified particles having diameters of 3µ or less, to separate out and deliver the second fraction into a collection container 80 for receiving product 2 comprising egg shell calcified particles having diameters in a range from about 3µ to about 7µ, and to separate the third fraction 90 comprising egg shell calcified particles having diameters larger than about 7µ into a conveyance equipment for delivery of the third fraction 90 back into the milling machine 50 for further milling and powderizing.

It is optional if so desired, to configure the membrane/shell separating equipment 20 to concentrate the separated membrane components and deliver the concentrated membrane components to a suitable product container 95.

It is to be noted that the systems disclosed herein may be configured as batch throughput systems wherein a selected batch size of waste egg shells is received and processed to output the first product, the second product, and optionally, the third product. Alternatively, the systems may be continuous throughput systems wherein a constant supply of waste egg shells is delivered to the first components and processed constantly to output the first product, the second product, and optionally the third product. Alternatively, the systems may be semi-continuous throughput systems wherein a constant supply of waste egg shells is delivered to the first components of the systems for an extended period of time, for example 2 h, 3, 4, 6, 8, 12, 18, and therebetween, during which time constant outputs of the first product, the second product, and optionally the third product are processed.

Another embodiment of the present disclosure pertains to an egg shell calcified particle product for use as a filler in coating compositions such as paints, sealers, and the like, wherein the egg shell calcified particles have diameters of 3µ or less, and wherein the egg shell calcified particle product is produced from waste egg shells using the system and/or methods disclosed herein.

Another embodiment of the present disclosure pertains to an egg shell calcified particle product for use as a filler in cosmetics topical compositions such as moisturizers, lotions, creams, facial scrubs, and the like, wherein the egg shell calcified particles have diameters of 3µ or less, and wherein the egg shell calcified particle product is produced from waste egg shells using the system and/or methods disclosed herein.

Another embodiment of the present disclosure pertains to an egg shell calcified particle product for use as a filler dental filling compositions, wherein the egg shell calcified particles have diameters of 3µ or less, and wherein the egg shell calcified particle product is produced from waste egg shells using the system and/or methods disclosed herein.

Another embodiment of the present disclosure pertains to an egg shell calcified particle product for use as an abrasive blasting media with abrasive blasting equipment compositions, wherein the egg shell calcified particles having diameters in a range from about 3µ to about 7µ, and wherein the egg shell calcified particle product is produced from waste egg shells using the system and/or methods disclosed herein.

EXAMPLE

The purpose of this study was to compare the performance of a waste egg shell calcified particle product as a calcium carbonate substitute in sealers used for coating concrete.

Waste egg shells were processed by the following method to produce a sample egg shell calcified particle product.

1. The membrane components of the waste egg shells were separated from the calcified outer shell components to produce de-membranized egg shell calcified components.
2. The de-membranized egg shell calcified components were washed to remove any remaining membrane components, and then were dried.

3. The dried de-membranized egg shell calcified components were milled in a laboratory-scale hammer mill to produce a powdered product comprising small-diameter egg shell calcified particles.
4. The powdered small-diameter egg shell calcified particles sieved to separate a fraction of particles having diameters of 3µ or less from the larger particles.
5. The milling and sieving steps were repeated until most of the milled egg shell calcified particles had diameters of 3µ or less.

Cement paving blocks having dimensions 12"×12"×1.5" (L, W, D) received one of the following coatings on their top surfaces: (i) coated with a commercial primer coating, (ii) coated with a commercial primer coating which was then overlaid with a coating mixture comprising calcium carbonate, (iii) coated with a commercial primer coating which was then overlaid with a coating mixture comprising the milled egg shell calcified particles, and (iv) no coating (control). Some of the concrete paving blocks were divided into two equal sections wherein one section was untreated and the other section was coated with a commercial primer coating which was then overlaid with a coating mixture comprising calcium carbonate. Other concrete paving blocks were divided into two equal sections wherein one section was untreated and the other section was coated with a commercial primer coating which was then overlaid with a coating mixture comprising the milled egg shell calcified particles.

The surfaces of the cement paving blocks were examined with optical coherence tomography (OCT) using a surface-scanning probe head comprising a light source focused through a lens having a 5-mm focal distance. The light back-scattered by the sample propagates back through the lens and toward the detection of the OCT system. The detected signal incoming from one single location of the focused probing beam was recorded and represents one depth scan. A full OCT image was obtained by scanning the lens from one point to the next, each time recording a depth scan corresponding to that specific location. Each OCT image acquired for this study (FIGS. 2-7) contained 6,000 depth scans, with the distance between two consecutive depth scans being 2.5 micrometers. The incoming probing beam approached the samples from the top in all cases.

In every OCT image from this study, the unit scale along the horizontal axis was 2.5 micrometers per pixel, and the unit scale along the vertical axis (depth axis) was 1.0 micrometers per pixel. Multiple OCT images were acquired from all samples in order to establish a pattern of consistency for each sample.

Figure 2:
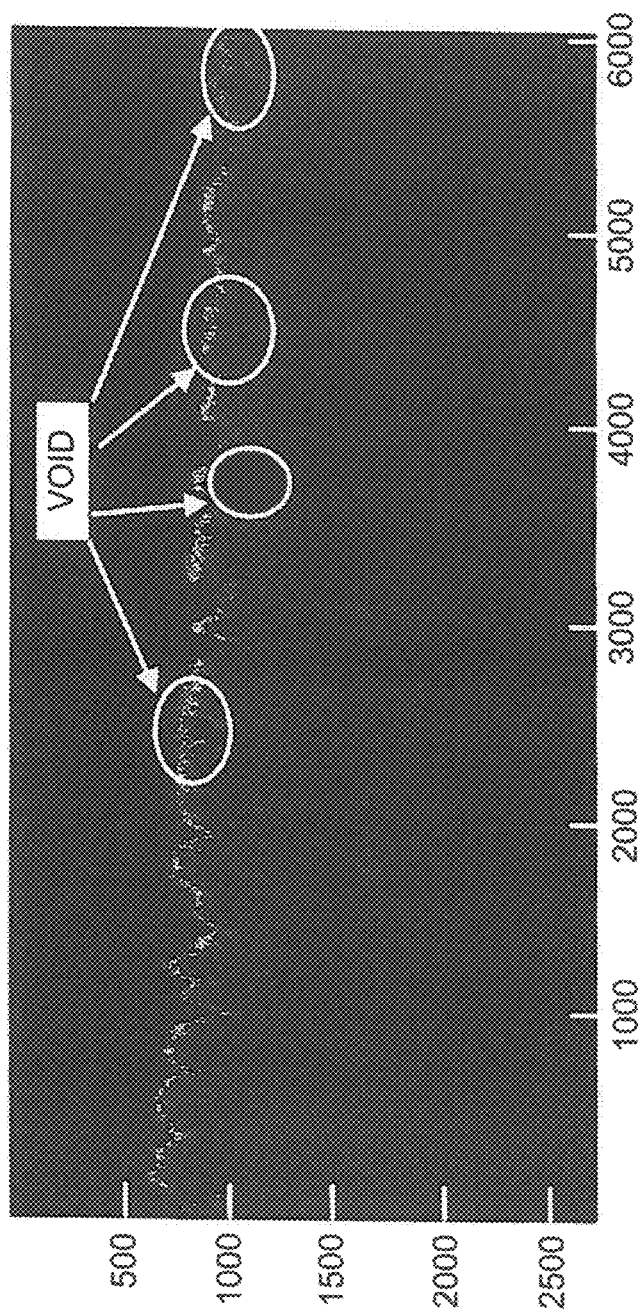
FIG. 2 is an optical coherence tomography (OCT) image of a side view of a section of uncoated concrete.

FIG. 2 shows an OCT image of the uncoated side of a concrete paving block. Details such as surface imperfections (pores) and empty pockets (voids) located under the concrete surface are clearly distinguishable.

Figure 3:
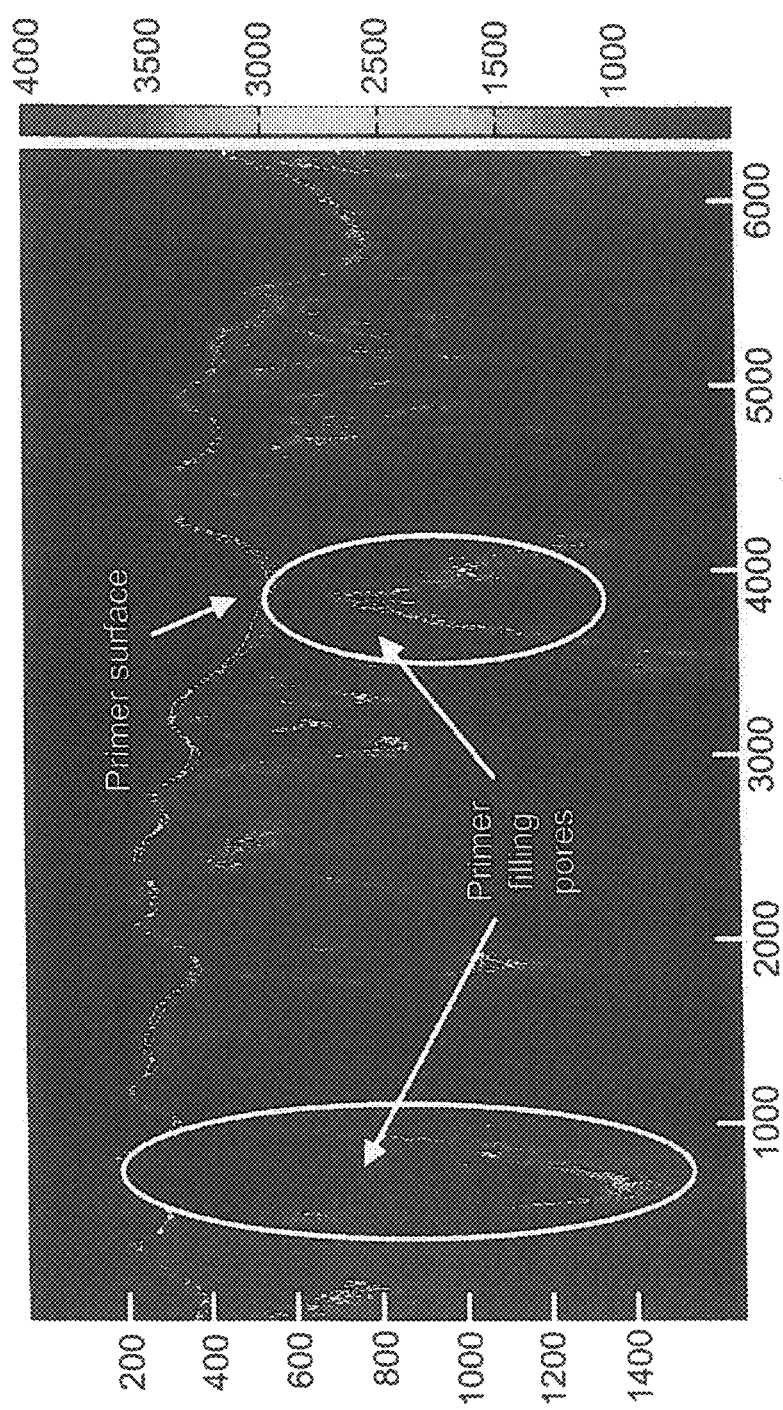
FIG. 3 is an OCT image of a side view of a section of concrete coated with a commercial primer composition.

FIG. 3 shows an OCT image of the primer layer applied over the porous surface of a concrete paving block. The intensity bar shown on the right has red corresponding to the strongest OCT signal and dark blue to the weakest signal recorded in the image. The air/primer interface is marked as "Surface". Clearly visible in FIG. 3 is how the primer filled the concrete pores and voids with two examples of filled voids encircled. The interfaces that mark the boundaries between the primer and concrete are also visible. A very good example of primer/concrete separation is marked to the right of FIG. 3 and shows one big void filled with primer whose volume is also split in two by a concrete peak. The primer thoroughly filled all the surface pores. Important to note in FIG. 3 is that the signal acquired from within the primer pockets which fill the concrete pores does not have a "spotty" (i.e. speckled) appearance, like the spotty appearance displayed by the signal acquired from within the concrete. This means that the primer is not only transparent but also does not scatter the probing light and this is how primer is differentiated from coating material in the OCT images.

Figure 4:
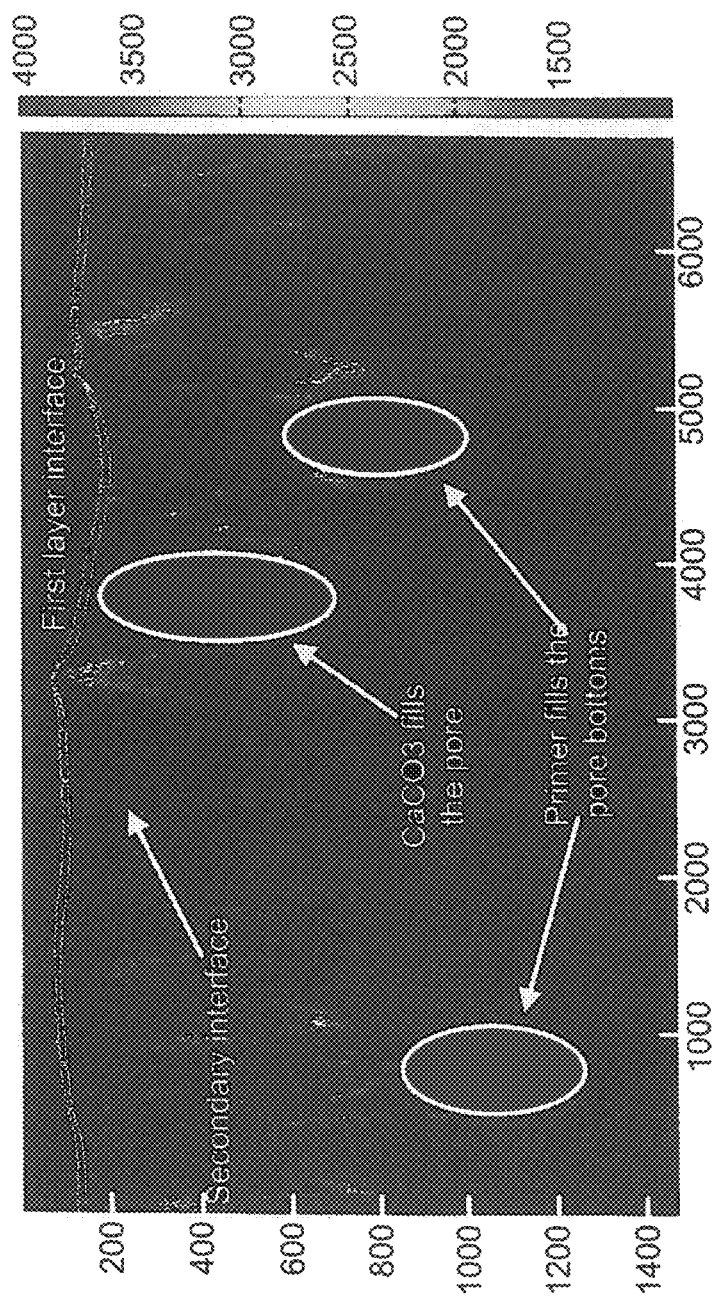
FIG. 4 is an OCT image of a side view of a section of concrete having a first coating with a commercial primer composition which was overlaid with a second coating containing calcium carbonate powder.

FIG. 4 shows the surface of a concrete paving block that received a calcium carbonate coating applied over the primer layer. "The first interface" (the air/coating interface) is obvious in the image. The image also shows clear differences between porous regions filled with calcium carbonate and the surrounding concrete matrix. For convenience, some of the pores filled with calcium carbonate are circled. It is noted that the speckles ("spots") of the signal acquired from regions with calcium carbonate are finer and look denser that the signal "spots" from regions with concrete. From the finer and dense speckle display we can conclude that the calcium carbonate particles distribute themselves quite homogeneous within the primer layer. In addition, it is possible to identify pools of primer which did not mix with calcium carbonate. Two such examples are circled. There are also "secondary interfaces" that can be distinguished within the calcium carbonate layer. One such example is also marked. Although of dim intensity, by looking carefully across this figure, other such secondary interfaces are also visible.

Figure 5:
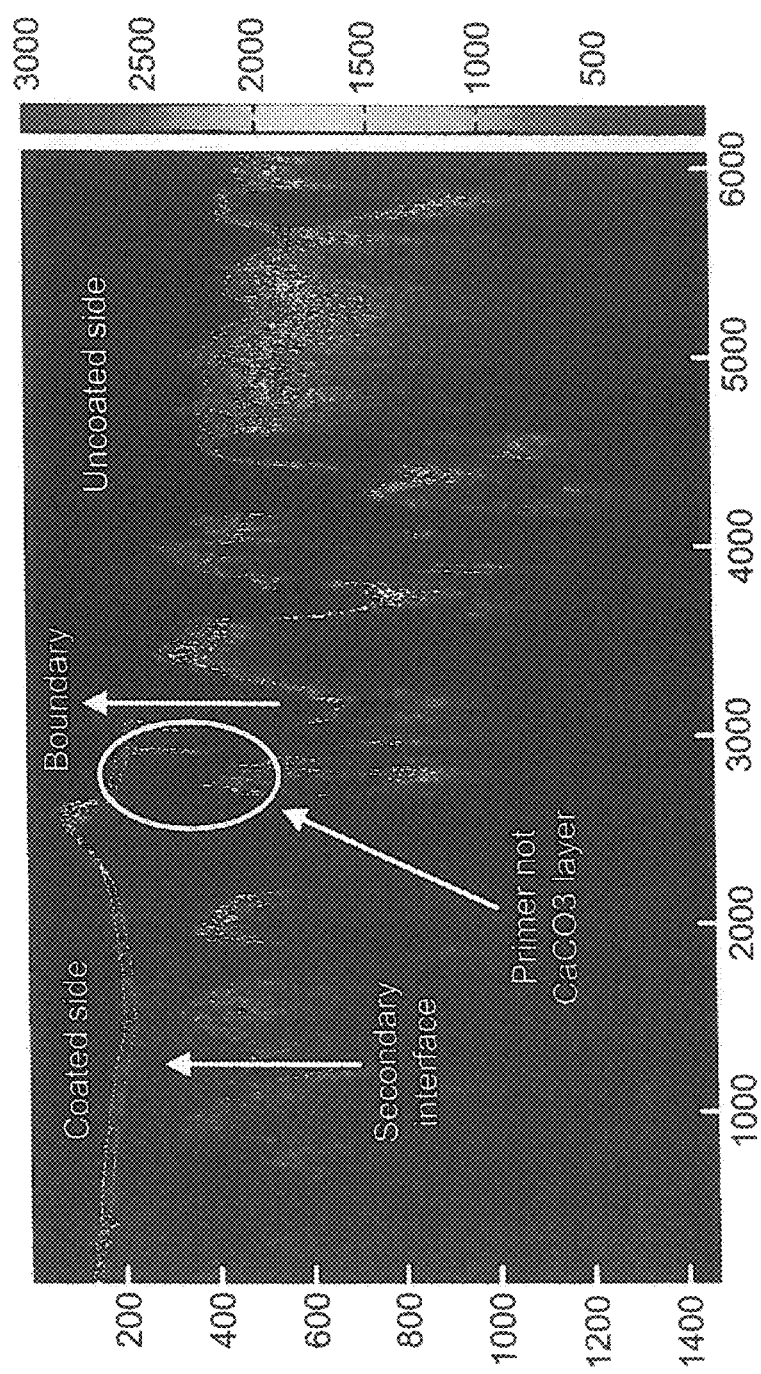
FIG. 5 is an OCT image of a side view of a section of concrete wherein the right side of the section was uncoated and the left side of the section received a first coating with a commercial primer composition which was overlaid with a second coating containing calcium carbonate powder.

FIG. 5 shows an OCT image of a region located at the boundary between uncoated and calcium carbonate-coated concrete. Features such as the "secondary Interfaces" observed in FIG. 4, are also visible on the coated side from FIG. 5. Pools of primer are also present at the bottom of some pores. Another detail in this image is the presence of a piece of un-mixed primer just at the coated/uncoated boundary labeled as "primer not CaCO3". This can be identified as primer due to the lack of the spotty pattern (i.e. speckle) which characterizes the OCT signal coming from locations with calcium carbonate.

Figure 6:
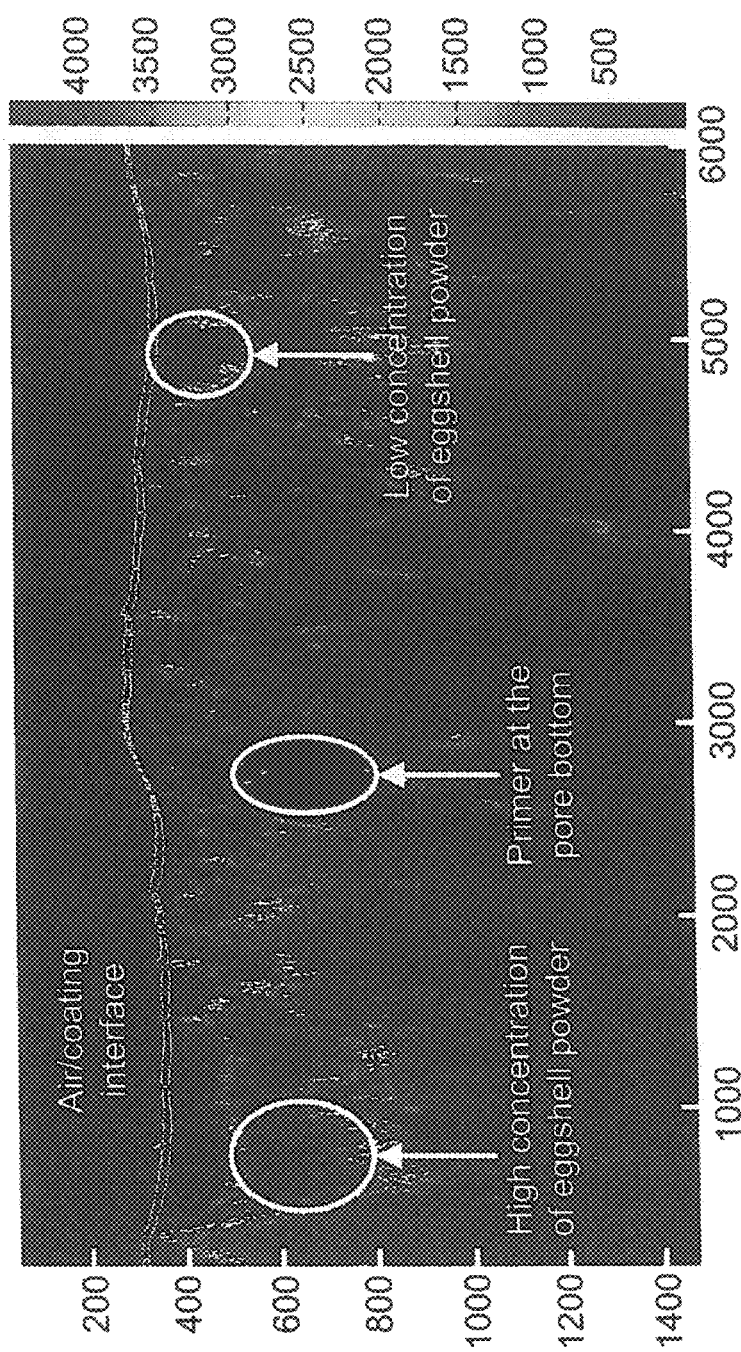
FIG. 6 is an OCT image of a side view of a section of concrete having a first coating with a commercial primer composition which was overlaid with a second coating containing egg shell calcified particles produced with a method disclosed herein.

FIG. 6 shows an OCT image acquired from a region coated with egg shell calcified particles/primer mix. There are some similarities with the calcium carbonate coating shown in FIG. 5, for example the interface separating the air from the coating, as well as the pools of primer from the bottom of some of the concrete surface pores. There are also some obvious differences between the two cases. Firstly, the particle density of eggshell coating is not uniform. Based on speckle densities observed across the eggshell layer, it can be can inferred that there are locations with high density and low density of particles across the coated region. It is also apparent that the adjacent regions with different eggshell calcified particles concentrations are separated by interfaces. There are two examples circled in FIG. 6, one marks a high-density region and the other marks a low-particle-density region. The low-density regions are located toward the surface of the coating, very near the air/coating interface and very often actually forms that interface. This indicates that the egg shell calcified particles diffuse deeper into the concrete pores, i.e. toward the bottom of the coating layer, during the time period before the layer solidifies.

Figure 7:
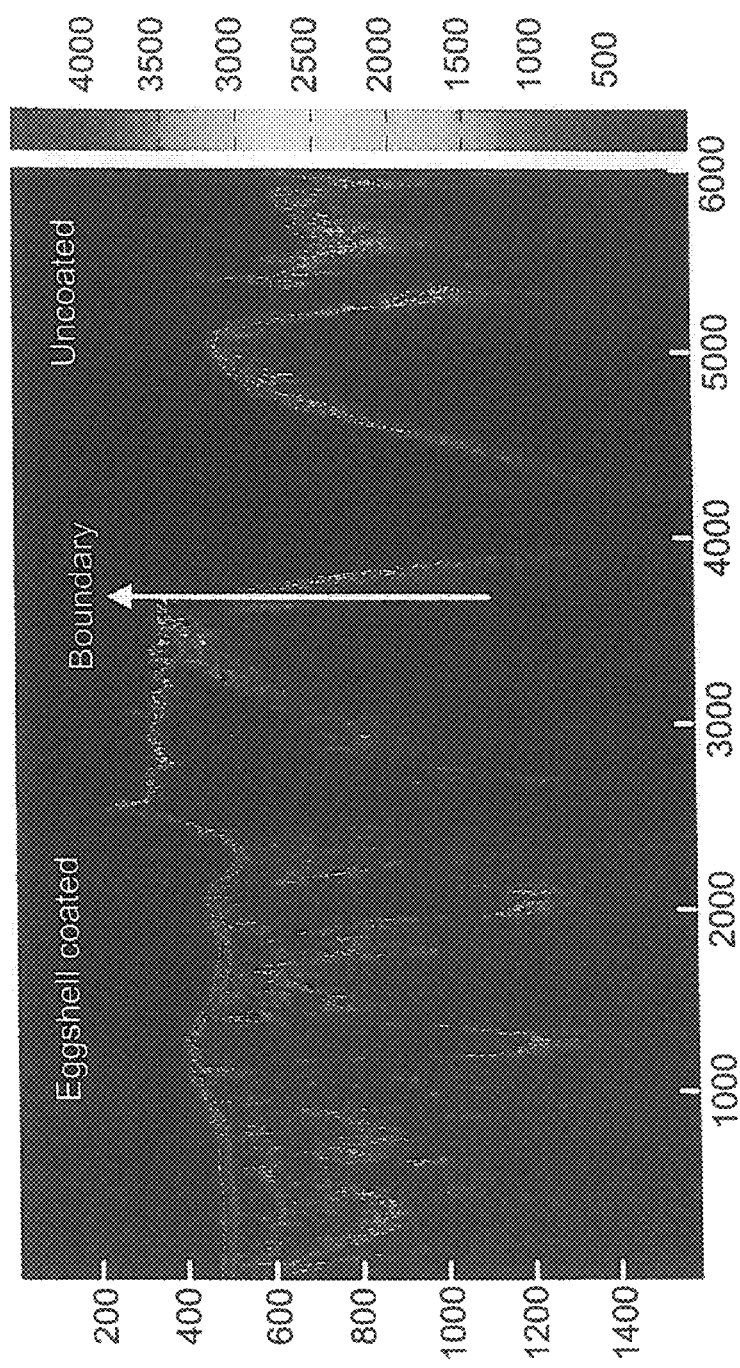
FIG. 7 is an OCT image of a side view of a section of concrete wherein the right side of the section was uncoated and the left side of the section received a first coating with a commercial primer composition which was overlaid with a second coating containing egg shell calcified particles produced with a method disclosed herein.

FIG. 7 shows an OCT image of a region located at the boundary of a concrete paving block between an uncoated surface and a surface coated with primer and egg shell calcified particles. The features observed and noted in FIG. 6 are also visible on the coated side of this concrete paving block.

Based on the comparisons of OCT images of concrete paving blocks coated with a primer and calcium carbonate with OCT images of concrete paving blocks coated with a primer and egg shell calcified particles, it is clear that calcium carbonate components of commercial sealers can be substituted for with egg shell calcified particles produced as disclosed herein.

The invention claimed is:
1. A product consisting of calcified de-membranized egg shell particles without membrane components, having diameters of 3µ or less.

* * * * *